(12) United States Patent
Loh et al.

(10) Patent No.: US 9,078,849 B2
(45) Date of Patent: Jul. 14, 2015

(54) PLANT EXTRACT COMPRISING STATINS AND PREPARATION TECHNIQUES AND USES THEREOF

(75) Inventors: Heng Meng Loh, Singapore (SG); Mun Kin Joel Lee, Singapore (SG); Pak Ho Henry Leung, Singapore (SG); Subramaniam Gurusamy, Singapore (SG); Wai To Fung, Singapore (SG)

(73) Assignees: Nanyang Polytechnic, Singapore (SG); Eu Yan Sang International Ltd., Singapore (SG)

( * ) Notice: Subject to any disclaimer, the term of this patent is extended or adjusted under 35 U.S.C. 154(b) by 394 days.

(21) Appl. No.: 13/263,035

(22) PCT Filed: Apr. 8, 2010

(86) PCT No.: PCT/SG2010/000142
§ 371 (c)(1),
(2), (4) Date: Dec. 22, 2011

(87) PCT Pub. No.: WO2010/117342
PCT Pub. Date: Oct. 14, 2010

(65) Prior Publication Data
US 2012/0093800 A1   Apr. 19, 2012

Related U.S. Application Data

(60) Provisional application No. 61/167,543, filed on Apr. 8, 2009.

(51) Int. Cl.
*A61K 36/062*     (2006.01)
*A61K 31/22*      (2006.01)
*A61K 31/365*     (2006.01)
*A61K 36/48*      (2006.01)
*A61K 36/899*     (2006.01)

(52) U.S. Cl.
CPC .............. *A61K 36/062* (2013.01); *A61K 31/22* (2013.01); *A61K 31/365* (2013.01); *A61K 36/48* (2013.01); *A61K 36/899* (2013.01)

(58) Field of Classification Search
IPC .............................. A61K 36/062,36/899, 31/22
See application file for complete search history.

(56) References Cited

U.S. PATENT DOCUMENTS 4,323,648 A   4/1982   Tanzawa et al.
5,202,029 A   4/1993   Haytko et al.
(Continued)

FOREIGN PATENT DOCUMENTS

WO   2005/104864 A1   11/2005

OTHER PUBLICATIONS

C. Lee, et al., "A Simple and Rapid Approach for Removing Citrinin while Retaining Monacolin K in Red Mold Rice," Journal of Argicultural and Food Chemistry (2007), vol. 55(26), pp. 11101-11108, 8 pages.

(Continued)

*Primary Examiner* — Rosanne Kosson
(74) *Attorney, Agent, or Firm* — Osha Liang LLP

(57) ABSTRACT

A plant extract comprising one or more statins and being substantially free of polar compounds that affect pharmacokinetics of a drug in a subject is provided. Also provided is a method of preparing an extract comprising the step of removing polar compounds that affect pharmacokinetics of a drug in a subject from a plant material containing one or more statins.

9 Claims, 6 Drawing Sheets

(56) References Cited

U.S. PATENT DOCUMENTS

| | | | |
|---|---|---|---|
| 6,387,258 | B1 | 5/2002 | Keri et al. |
| 6,849,281 | B2 * | 2/2005 | Bodor et al. .................. 426/46 |
| 2004/0018210 | A1 | 1/2004 | Hajjaj et al. |
| 2006/0058261 | A1 | 3/2006 | Aube |
| 2007/0218185 | A1 | 9/2007 | Beindorff et al. |

OTHER PUBLICATIONS

T. Wang, et al., "Monascus Rice Products," Advances in Food and Nutrition Research (2007), vol. 53, pp. 123-159, 37 pages.
International Search Report issued in PCT/SG2010/000142, mailed on Jun. 30, 2010, 3 pages.
Written Opinion of the International Search Authority issued in PCT/SG2010/000142, mailed on Jun. 30, 2010, 6 pages.
Written Opinion of the International Preliminary Examining Authority issued in PCT/SG2010/000142, mailed on Mar. 3, 2011, 7 pages.
International Preliminary Report on Patentability issued in PCT/SG2010/000142, completed on May 20, 2011, 14 pages.
Office Action issued in counterpart Japanese application No. 2012-504659, mailed Mar. 4, 2014 (4 pages), English translation only was considered.
Lee, Chun-Lin et al; "A simple and rapid approach for removing citrinin while retaining monacolin K in red mold rice," Journal of Agricultural and Food Chemistry, vol. 55, No. 26, pp. 11101-11108 (2007) (8 pages).
Wang, Tseng-Hsing et al.; "Monascus Rice Products," Advances in Food and Nutrition Research, vol. 53, pp. 123-159 (2007) (37 pages).
Search Report issued in corresponding European Application No. 10761948.8, mailed Jul. 25, 2013 (8 pages).
Yii-Lih Lin et al.; "Biologically active components and nutraceuticals in the Monascus-fermented rice: a review"; Applied Microbiology and Biotechnology, Springer, vol. 77, No. 5; Nov. 22, 2007 (9 pages).
Mee Young Hong et al.; "Anticancer effects of Chinese red yeast rice versus monacolin K alone on colon cancer cells"; Journal of Nutritional Biochemistry, Butterworth Publishers, vol. 19, No. 7; Jul. 1, 2008 (11 pages).
Wai to Fung et al.; "Assessment of Extracts from Red Yeast Rice for Herb-Drug Interaction by in-vitro and in-vivo assays"; Scientific Reports, vol. 2; Mar. 2, 2012 (6 pages).
English Translation for JP2001-270834 (11 pages), Jan. 2015.
English translation for Examination Report issued in corresponding Tawainese Application No. 099110875, mailed Jul. 22, 2014 (1 page).

* cited by examiner

PLANT EXTRACT COMPRISING STATINS AND PREPARATION TECHNIQUES AND USES THEREOF

TECHNICAL FIELD

The present invention generally relates to plant extracts containing statins. The present invention also relates to a method of obtaining such an extract and its use.

BACKGROUND

Herbal supplements are well known and have been used to supplement traditional dietary and medical regimens. Typically such supplements are in the form of extracts which are believed to provide health and medicinal benefits including the prevention and treatment of disease.

Many plants which are used in the manufacture of extracts are known to synthesize chemicals that are useful in the maintenance of health in humans. However, despite the increase in the use of such extracts the understanding of plant-drug interactions is still in its infancy. This lack of understanding of such interactions can lead to adverse reactions which can be life-threatening or, in a worst case scenario, fatal.

Furthermore, the precise composition of such extracts has not been fully defined and as such many plant extracts may contain compounds that can adversely affect drug kinetics in a subject.

For example, a popular plant extract is red yeast rice. This extract has many uses including food coloring and as an ingredient in rice wine. More recently red yeast rice extract has been used to lower lipids and cholesterol levels. However, the known extracts of red yeast rice contain significant amounts of contaminants.

Accordingly, the removal of one or more of these contaminants would be advantageous in increasing both consumer confidence as to the precise contents of the extract and providing regulatory authorities with accurate data regarding the composition of the extract.

There is a need to provide a plant extract having a reduced amount of contaminants that overcomes, or at least ameliorates, one or more of the disadvantages described above.

There is a need to provide a plant extract having a reduced amount of contaminants having an adverse effect on pharmacokinetics of a drug in a subject.

SUMMARY

According to a first aspect, there is provided a plant extract comprising one or more statins and being substantially free of polar compounds.

According to a second aspect, there is, provided a plant extract comprising one or more statins and being substantially free of polar compounds that affect pharmacokinetics of a drug in a subject.

According to a third aspect, there is provided a method of preparing an extract comprising the step of removing polar compounds from a plant material wherein said plant material contains one or more statins.

According to a fourth aspect, there is provided a method of preparing a plant extract comprising the step of removing one or more polar compounds that affect pharmacokinetics of a drug in a subject from said plant extract.

Advantageously, the removal of one or more polar compounds from the plant extract substantially reduces adverse or unwanted drug-herb interactions.

It is a further advantage of the method of the disclosure to provide a consistent effective amount of one or more statins in the plant extract.

According to a fifth aspect, there is provided a composition comprising a plant extract according to the first aspect or the second aspect, together with a pharmaceutically acceptable carrier.

According to a sixth aspect, there is provided a dosage form comprising a plant extract according to the first aspect or the second aspect, together with a pharmaceutically acceptable carrier.

According to a seventh aspect, there is provided use of a plant extract according to the first aspect or the second aspect in the manufacture of a medicament for the treatment or prevention of hyperlipidemia.

According to an eighth aspect, there is provided, use of a plant extract according to the first aspect or the second aspect in the manufacture of a medicament for the reduction of cholesterol in a subject.

According to a ninth aspect, there is provided a packaged dosage form comprising a plant extract according to the first aspect or the second aspect together with instructions for use.

According to a tenth aspect, there is provided use of a plant extract according to the first aspect or the second aspect in the manufacture of a medicament for the inhibition of 3-hydroxy-3-methylglutaryl-coenzyme A (HMG-CoA) reductase in a subject.

According to an eleventh aspect, there is provided a method of preparing a plant extract comprising, in sequence, the steps of:
 removing one or more toxins from a plant material;
 removing one or more polar compounds from the plant material;
 forming an extract from the plant material.

DETAILED DESCRIPTION

Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The term "pharmacokinetics" is to be interpreted broadly to include the action of administered drugs within the human or animal body. In particular this term refers to drug absorption, distribution, metabolism, and excretion; onset of action; duration of effect; biotransformation; effects and routes of excretion of the metabolites of the drug.

The terms "polar compound", "polar compounds" and grammatical variations thereof, in the context of this specification, refers to compounds, typically organic compounds, in the plant extract which, as a whole, have a non-zero dipole moment.

The term "naturally occurring" in the context of this specification, refer to compounds, such as statins, which occur naturally in a plant material.

The term "plant material" is to be construed broadly to include all members of the Plantae kingdom, Fungi kingdom and algae. The plant material may comprise a solid mass or an extract solution of the plant material.

In the context of this disclosure the term "administering" and variations of that term including "administer" and "administration", includes contacting, applying, delivering or providing a compound or composition of the invention to an organism, or a surface by any appropriate means.

In the context of this disclosure, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the terms "therapeutically effective amount" includes a sufficient but non-toxic amount of a compound or composition of the disclosure to provide the desired therapeutic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

In the context of this specification, the term "subject" includes humans and individuals of any species of social, economic or research importance including but not limited to members of the genus ovine, bovine, equine, porcine, feline, canine, primates (including human and non-human primates), rodents, murine, caprine, leporine, and avian.

"Dosage form" as used herein refers to physically discrete units suited as unitary dosages for the individual to be treated; each unit containing a predetermined quantity of plant extract is calculated to produce the desired therapeutic effect in association with the required pharmaceutical carrier. The plant extract may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The language "pharmaceutically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated The word "substantially" does not exclude "completely" e.g. a composition which is "substantially free" from Y may be completely free from Y. Alternatively, the composition may still contain from 1-10% of Y. Where necessary, the word "substantially" may be omitted from the definition of the invention.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

Disclosure of Optional Embodiments

Exemplary, non-limiting embodiments of a plant extract comprising one or more statins, will now be disclosed.

The plant extract is substantially free of polar compounds that affect pharmacokinetics of a drug in a subject.

In one embodiment the one or more statins are naturally occurring statins and may be selected from the group consisting of lovastatin, simvastatin, pravastatin and mevastatin.

Preferably, the one or more lovastatins are selected from one or more monacolins. In a preferred embodiment the one or more monacolins are selected from the group consisting of monacolin K, monacolin J, monacolin L and monacolin M. Preferably, the one or more monacolins are selected from monacolin K and monacolin J. In a most preferred embodiment the monacolin is monacolin K.

In another embodiment the monacolin K is present in the plant extract in an amount in the range selected from the group consisting of about 0.01-500 mg; about 0.1-400 mg; about 0.2-300 mg; about 0.2-200 mg; about 0.2-100 mg; about 0.2-50 mg; about 0.2-25 mg; about 0.2-10 mg; about 0.2-5 mg and about 0.2-2 mg per gram of plant extract. Preferably, the monacolin K is present in the plant extract in an amount of from 0.2 mg-1 mg per gram of extract.

In another embodiment, the plant extract is a product of microbial fermentation. Preferably, the microorganism used in the microbial fermentation is *Monascus purpureus*. Alternatively, the microorganism used in the microbial fermentation is selected from *Monascus ruber* and *Monascus pilosus*.

In one embodiment the plant extract is extracted from a plant belonging to the family Poaceae.

In a preferred embodiment the plant is a cereal selected from the group consisting of maize, rice, wheat, barley, sorghum, millet, oat, rye, triticale and buckwheat.

Alternatively, the plant is selected from the family Fabaceae. In a preferred embodiment the plant is a bean selected from the genus *Phaseolus*. Preferably, the bean may be selected from the group consisting of *P. vulgaris, P. filiformis, P. coccineus, P. lunatus, P. maculatus* and *P. acutifolius*.

In a further preferred embodiment, the cereal is rice. Preferably, the rice is red yeast rice.

In another embodiment, the plant extract is extracted from a fungi. Preferably, the fungi is a *pleurotus* fungi. Preferably, the *pleurotus* fungi is *Pleurotus ostreatus*.

In one embodiment, at least 50% of the polar compounds are removed from said extract. Preferably, at least 60%, or at least 70%, or at least 80%, or at least 90% of the polar compounds are removed from said extract. Most preferably, at least 95% of the polar compounds are removed from said extract. Alternatively, the plant extract may have as much as 0.26 g of polar compounds removed per gram of plant extract.

In one embodiment, the plant extract has less than 30% by weight polar compounds, preferably less than 25% by weight polar compounds, preferably less than 20% by weight polar compounds, preferably less than 15% by weight polar compounds, preferably less than 10% by weight polar compounds, preferably less than 5% by weight polar compounds, preferably less than 4% by weight polar compounds, preferably less than 3% by weight polar compounds, preferably less than 2% by weight polar compounds, preferably less than 1% by weight polar compounds, preferably less than 0.5% by weight polar compounds.

There is also provided a method of preparing an extract comprising the step of removing polar compounds from a plant material wherein said plant material contains one or more statins.

There is also provided a method of preparing an extract comprising the step of removing one or more polar compounds that affect pharmacokinetics of a drug in a subject from a plant material containing one or more statins.

In one embodiment the plant material is solid plant matter.

In another embodiment, the size of the plant material is selected from the range consisting of about 0.1 cm-1 cm; about 0.2-0.9 cm and 0.3-0.9 cm. Preferably, the size of the plant material is 0.3-0.9 cm.

In one embodiment the plant material may be ground prior to preparing the extract.

Preferably the particle size of the ground plant material is selected from the range consisting of about 0.1 mm-2 mm; about 0.2 mm-1 mm; about 0.3 mm-1 mm; about 0.4 mm-1 mm and about 0.5-1 mm. Preferably, the particle size of the ground plant material is 0.5-1 mm.

In an optional embodiment, the ground plant material may be sonicated prior to preparation of the extract.

In one embodiment, the method further comprises the step of removing one or more toxins, including citrinin and tannins, from the plant material prior to the step of removing said one or more polar compounds.

In one embodiment, the one or more toxins are removed by exposing the plant material to a solvent selected to dissolve said one or more toxins. In one embodiment, the solvent for dissolving said one or more toxins is slightly acidic, that is the pH of the solvent for dissolving said one or more toxins is between about 5 to less than 7, more preferably about 6 to less than 7, yet more preferably about 6.5 to less than 7. Preferably, the solvent comprises a salt such as an organic salt of an alkaline metal. Exemplary salts may be selected from the group consisting of sodium phosphate, sodium acetate and sodium bicarbonate. Furthermore, an organic acid may also be present in said solvent for dissolving said one or more toxins.

The organic acid is preferably a carboxylic acid. Most preferably the carboxylic acid is acetic acid.

Suitable concentrations of the salt solution are selected from the group consisting of 0.05M, 0.1M, 0.15M and 0.2M. Preferably, the salt solution comprises 0.1M sodium acetate. The acetic acid is preferably a 0.5% solution.

In a preferred embodiment the amount of salt solution used is in the range selected from the group consisting of 0.5 ml/g; 1 ml/g; 1.5 ml/g; 2 ml/g; 2.5 ml/g; 3 ml/g; 3.5 ml/g; 4 ml/g; 4.5 ml/g; 5 ml/g; 5.5 ml/g; 6 ml/g; 6.5 ml/g; 7 ml/g; 7.5 ml/g; 8 ml/g; 8.5 ml/g; 9 ml/g; 9.5 ml/g and 10 ml/g of plant material. Preferably, the amount of salt solution used is 4 ml/g of plant material.

In one embodiment the step of exposing the plant material to a solution comprising one or more of a salt and an organic acid is undertaken for about 8-36 hours at a temperature of 20-60° C. Most preferably, the plant material is exposed for a period selected from the group consisting of about 8-34 hours, about 10-32 hours, about 12-30 hours, about 14-28 hours, about 16-26 hours, about 18-26 hours, about 20-26 hours and about 22-26 hours. In a most preferred embodiment the plant material is exposed to the solution comprising one or more of a salt and an organic acid for 12 hours.

In another embodiment the plant material is exposed to the solution comprising one or more of a salt and an organic acid at a temperature of 20-60° C. Preferably the plant material is exposed at a temperature selected from the group consisting of 21-55° C., 22-50° C., 23-45° C., 24-40° C. 25-35° C., 25-30° C. In a most preferred embodiment the plant material is exposed to the solution comprising one or more of a salt and an organic acid at a temperature of 23° C. for 12 hours.

Preferably, the extract has less than 500 µg, more preferably, less than 450 µg, more preferably less than 400 µg, more preferably less than 350, more preferably less than more preferably less than 300 µg, more preferably less than 250 µg more preferably less than 200 µg, more preferably less than 150 µg, more preferably less than 100 µg of citrinin per gram of red yeast rice extract. In a most preferred embodiment the extract has a level of citrinin between 332 µg and 133 µg of citrinin per gram of the red yeast rice extract.

In one embodiment, the plant material, once the one or more toxins have been removed, is exposed to an aqueous solution for about 8-36 hours at a temperature of 20-60° C. to remove one or more polar compounds. Most preferably, the plant material is exposed to the aqueous solution for a period selected from the group consisting of about 8-34 hours, about 10-32 hours, about 12-30 hours, about 14-28 hours, about 16-26 hours, about 18-26 hours, about 20-26 hours and about 22-26 hours. In a most preferred embodiment the plant material is exposed to the aqueous solution for 12 hours.

In another embodiment the plant material is exposed to an aqueous solution at a temperature of 20-60° C. Preferably the plant material is exposed to the aqueous solution at a temperature selected from the group consisting of 21-55° C., 22-50° C., 23-45° C., 24-40° C. 25-35° C., 25-30° C. In a most preferred embodiment the plant material is exposed to the aqueous solution at a temperature of 23° C. for 12 hours.

In a preferred embodiment the amount of aqueous solution used is in the range selected from the group consisting of 0.5 ml/g; 1 ml/g; 1.5 ml/g; 2 ml/g; 2.5 ml/g; 3 ml/g; 3.5 ml/g; 4 ml/g; 4.5 ml/g; 5 ml/g; 5.5 ml/g; 6 ml/g; 6.5 ml/g; 7 ml/g; 7.5 ml/g; 8 ml/g; 8.5 ml/g; 9 ml/g; 9.5 ml/g and 10 ml/g of plant material. Preferably, the amount of aqueous solution used is 4 ml/g of plant material.

In a most preferred embodiment, the aqueous solution is water.

Advantageously, this step not only removes the polar compounds but also removes any residual salt solution present in the plant material.

Without wishing to be bound by any particular theory it is believed that the one or more polar compounds present in the plant extract interfere with the pharmacokinetics of administered drugs by inhibiting certain enzymes in a subject. It is believed that these enzymes include, but are not limited to, cytochrome P450, including subtypes 1A2, 2C9 and 3A4; and p-glycoprotein. P-glycoprotein is an ATP-dependent efflux pump with broad substrate specificity. P-glycoprotein transports various substrates across the cell membrane including drugs such as colchicine, tacrolimus and quinidine; chemotherapeutic agents such as etoposide, doxorubicin, and vinblastine; lipids, steroids, xenobiotics, peptides, bilirubin, cardiac glycosides like digoxin, immunosuppressive agents, glucocorticoids like dexamethasone and HIV-type 1 antiretroviral therapy agents like protease inhibitors and non-nucleoside reverse transcriptase inhibitors. Thus, removal of the polar compounds reduces the incidence of adverse drug-herb interactions.

Accordingly, in a preferred embodiment, the one or more polar compounds affect the pharmacokinetics of an administered drug by interacting with cytochrome P450 and p-glycoprotein.

Without wishing to be bound by any particular theory, it is believed that the polar compounds affect the pharmacokinetics of an administered drug by binding to cytochrome P450 and/or p-glycoprotein.

In another embodiment, the method further comprises the step of forming a liquid extract from said solid plant material.

Preferably the plant material, once the one or more polar compounds have been removed, is exposed to an organic solution for about 8-36 hours at a temperature of 20-50° C. Most preferably, the plant material is exposed to the organic solution for a period selected from the group consisting of about 8-34 hours, about 10-32 hours, about 12-30 hours, about 14-28 hours, about 16-26 hours, about 18-26 hours, about 20-26 hours and about 22-26 hours. In a most preferred embodiment the plant material is exposed to the organic solution for 12 hours.

In another embodiment the plant material is exposed to the organic solution at a temperature of 20-50° C. Preferably the plant material is exposed to the organic solution at a temperature selected from the group consisting of 21-50° C., 22-45° C., 23-40° C. 24-35° C., 25-30° C. In a most preferred embodiment the plant material is exposed to the organic solution at a temperature of 25° C. for 12 hours.

In a preferred embodiment the amount of organic solution used is in the range selected from the group consisting of 0.5 ml/g; 1 ml/g; 1.5 ml/g; 2 ml/g; 2.5 ml/g; 3 ml/g; 3.5 ml/g; 4 ml/g; 4.5 ml/g; 5 ml/g; 5.5 ml/g; 6 ml/g; 6.5 ml/g; 7 ml/g; 7.5 ml/g; 8 ml/g; 8.5 ml/g; 9 ml/g; 9.5 ml/g and 10 ml/g of plant material. Preferably, the amount of organic solution used is 4 ml/g of plant material.

In one embodiment the organic solution is selected from the group consisting of alcohols, ethers, haloforms, ketones and alkylene glycol. Preferably the organic solution comprises an organic compound that is miscible with water. The organic solution may comprise at least 50% organic compound in water. Preferably, the organic solution comprises at least 70% organic compound in water. In a preferred embodiment, the organic solution is an alcohol. Most preferably the alcohol is 70% ethanol.

In a further preferred embodiment, the method comprises the step of separating the plant material from the liquid extract and evaporating the solvent of the liquid extract to form a dried plant extract.

Preferably, the extraction solution is evaporated using a rotary evaporator.

Agitation may be preferably employed to increase the efficiency of the extraction method. Agitation may be performed at one of more of the steps of the extraction method. Preferably, the agitation is provided by sonication.

In another embodiment there is provided a composition comprising a plant extract according to the disclosure, together with a pharmaceutically acceptable carrier.

In yet another embodiment there is provided a dosage form, comprising a plant extract according to the disclosure, together with a pharmaceutically acceptable carrier.

In accordance with the present disclosure, the plant extract may be administered alone. Alternatively, the extract may be administered as a pharmaceutical, nutraceutical, veterinarial, agricultural, or industrial formulation which comprises at least one plant extract according to the invention.

The plant extract may be used in combination with other known treatments, including antifungal treatments, antibiotics, chemotherapeutic agents, etc. Suitable agents are listed, for example, in the Merck Index, *An Encyclopaedia of Chemicals, Drugs and Biologicals,* 12$^{th}$ Ed., 1996, the entire contents of which are incorporated herein by reference.

Combinations of active agents, including plant extracts of the invention, may be synergistic.

Convenient modes of administration include oral administration, inhalation, transdermal application, topical creams or gels or powders, or rectal administration. Preferably, the extract is administered orally.

Depending on the route of administration, the formulation and/or extract may be coated with a material to protect the compound from the action of enzymes, acids and other natural conditions which may inactivate the therapeutic activity of the compound. Such coatings, for example enteric coatings, are well known to those of skill in the art.

Dispersions of the plant extract may also be prepared in glycerol, liquid polyethylene glycols, and mixtures thereof and in oils. Under ordinary conditions of storage and use, pharmaceutical preparations may contain a preservative to prevent the growth of microorganisms.

In one embodiment, the plant extract may be administered orally, for example, with an inert diluent or an assimilable edible carrier. The plant extract and other ingredients may also be enclosed in a hard or soft shell gelatin capsule, compressed into tablets, or incorporated directly into an individual's diet. For oral therapeutic administration, the plant extract may be incorporated with excipients and used in the form of ingestible tablets, buccal tablets, troches, capsules, elixirs, suspensions, syrups, wafers, and the like. Suitably, such compositions and preparations may contain at least 1% by weight of the plant extract. Alternatively, the compositions and preparations of the plant extract may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of plant extract in therapeutically useful compositions is such that a suitable dosage will be obtained.

Supplementary active compounds may also be incorporated into the compositions according to the present invention.

In one embodiment, the carrier may be an orally administrable carrier.

Another form of a pharmaceutical composition is a dosage form formulated as enterically coated granules, tablets or capsules suitable for oral administration.

Also included in the scope of this invention are delayed release formulations.

Tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the analogue can be incorporated into sustained-release preparations and formulations.

Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the pharmaceutical compositions according to the invention may be carried out. One skilled in the art would be able, by routine experimentation, to determine effective, non-toxic dosage levels of the plant extract and/or composition and an administration pattern.

Further, it will be apparent to one of ordinary skill in the art that the optimal course of treatment, such as the number of doses of the plant extract or composition given per day for a defined number of days, can be ascertained using conventional course of treatment determination tests.

Generally, an effective dosage of the plant extract per 24 hours may be in the range of about 0.0001 mg to about 1000 mg per kg body weight; suitably, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

There is provided the use of the plant extract according to the disclosure in the manufacture of a medicament for the treatment or prevention of hyperlipidemia.

There is provided the use of the plant extract according to the disclosure in the manufacture of a medicament for the reduction of cholesterol in a subject.

There is provided the use of the plant extract according to the disclosure in the manufacture of a medicament for the reduction of cholesterol in a subject.

There is provided the use of the plant extract according to the disclosure in the manufacture of a medicament for the inhibition of 3-hydroxy-3-methylglutaryl-coenzyme A (HMG-CoA) reductase in a subject.

There is also provided a packaged dosage form comprising a plant extract according to the disclosure together with instructions for use.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

EXAMPLES

Figure 1A:
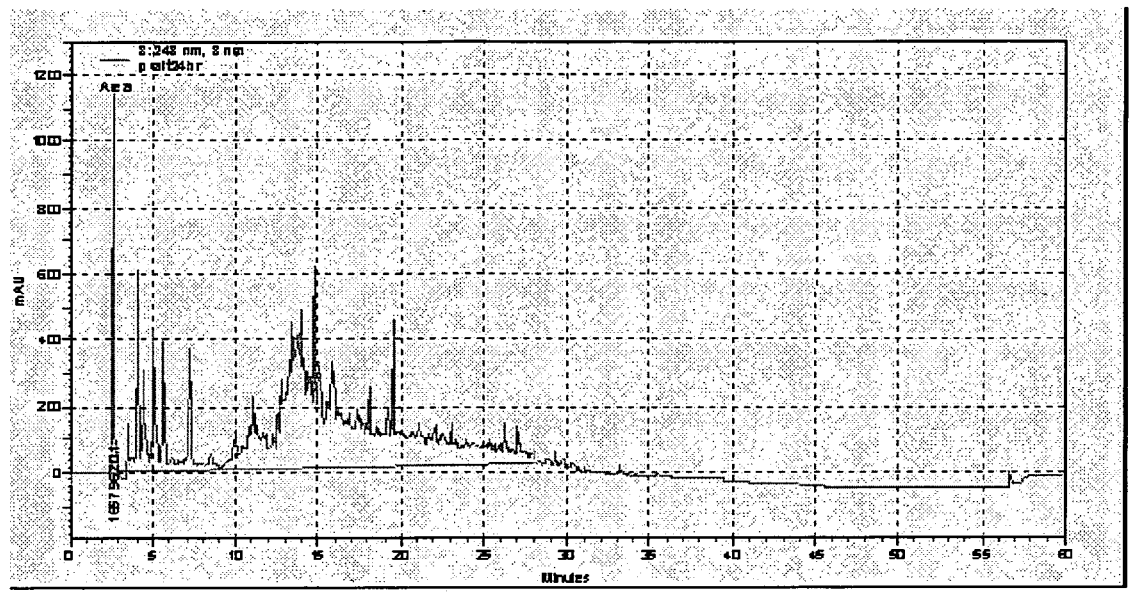
FIG. 1a shows a HPLC profile of a red yeast rice extract before removal of the polar compounds.

Non-limiting examples of the invention, including the best mode, and a comparative example will be further described in greater detail by reference to specific Examples, which should not be construed as in any way limiting the scope of the invention.

Example 1

Fermentation of Red Yeast Rice (RYR)

Preparation Method:
1. Rice (*Oryza sativa* var. *Japonica*) was soaked in water (4 ml/g) for 1 hr at 23° C.
2. The rice was then kept in an oven at 100° C. for 2 hours.
3. 5% (w/w) of *M. purpureus* was then added.
4. The rice was then incubated at 24-30° C. for 7-14 days with physical stirring every 2 days.

Example 2

Extraction Method

1. Whole red yeast rice (RYR) was exposed at 23° C. to 0.1M sodium acetate (4 ml/g of red yeast rice) for 12 hrs. This step was used to remove citrinin and other toxins from the RYR. The salt solution was then removed by filtration on filter paper or cheesecloth
2. The RYR extract was then exposed to water (4 ml/g of red yeast rice) at 23° C. for 12 hours. This step removes the polar compounds and any residual salt solution in the RYR preparation from step 1 above. The salt solution was then removed by filtration on filter paper or cheesecloth.

3. Finally, the last extraction step used 70% ethanol (4 ml/g of red yeast rice) at 23° C. for 12 hrs to produce an enriched monacolin K RYR extract.

Details of Final Extraction

The citrinin level was 0.3-0.7 μg/g of red yeast rice extract.

The percentage of the polar compounds removed by the extraction method is approximately 94.5%. A high performance liquid chromatography (HPLC) chromatograph of the dried extract is shown in FIG. 1. The conditions of the HPLC are: 3 μm pore size column, two solvents, solvent A 0.01% formic acid & solvent B 100% acetonitrile; a flow rate of 0.7 ml/min; gradient flow such that at 0 minutes solvent A is 97%, and at 50 minutes solvent B is 100%. Peaks falling within the area from 0 minutes to 10 minutes would indicate the presence of polar compounds in the dried extract.

As can be seen from the HPLC chromatograph in FIG. 1a, the RYR material prior to treatment with water contains polar fractions as shown in the area indicated by 165896201.

Figure 1B:
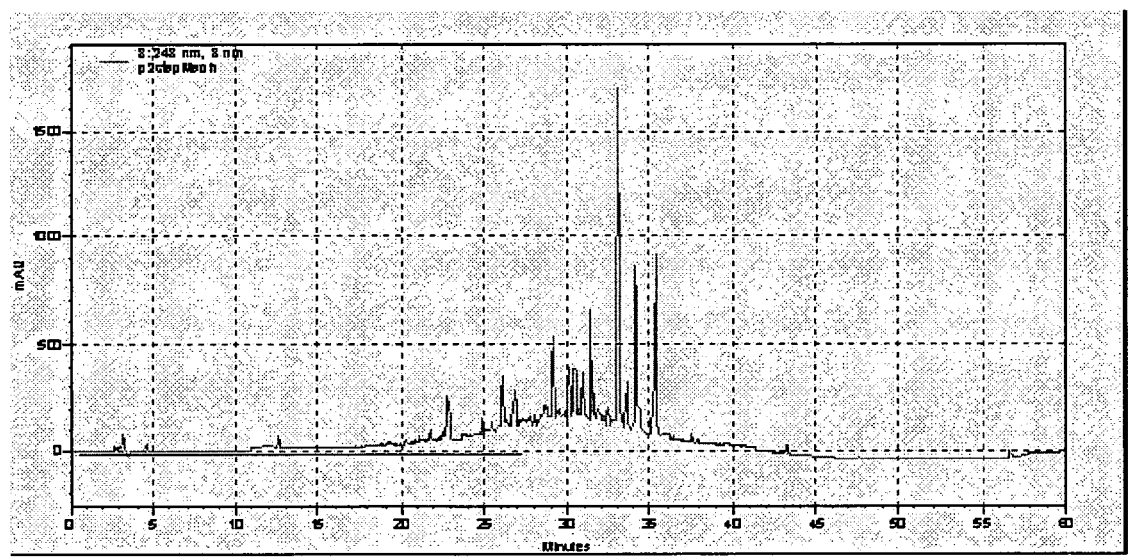
FIG. 1b is a HPLC profile of the dried red yeast rice extract, after removal of the polar compounds, obtained in accordance with the method of the disclosure.

FIG. 1b demonstrates that the RYR after treatment with water has a substantially reduced polar fraction shown by the area indicated by 9534468 (shown as a red line on FIG. 1b). The absence of peaks in this area indicates the removal of polar compounds from the R material. This indicates that approximately 95% of the polar compounds have been removed from the RYR material after treatment with water.

Monacolin K (lovastatin) level was 0.5-2 mg/g of red yeast rice extract.

Example 3

Pharmacokinetic Validation on RYR Extract

Cytochrome (CYP) P-450 Inhibition Study

CYP1A2A, CYP2C9 and CYP3A4 activity assays (CYP1A2, CYP2C9 and CYP3A4 P450-Glo™, Promega) employing luminogenic P450 probe substrates that are derivatives of beetle luciferin, a substrate for luciferase enzymes were used. The derivatives are not substrates for luciferase but are converted by CYP to luciferin, which in turn reacts with luciferase to produce a measurable amount of light that is directly proportional to the P450 activity.

The CYP membrane was treated with 20 μl of Luciferin-free water (untreated control), naringenin (CYP inhibitor, negative control) or the RYR water extract at different concentrations (1.25 mg/ml, 2.5 mg/ml and 5 mg/ml, drug treated) in a white opaque 96-well plate (Costar). The plate was pre-incubated at 37° C. for 10 min and then the reactions were started by addition of NADPH regeneration solution and incubated at 37° C. for 20 min. The reactions were then stopped, and detection of luminescence was initiated by adding an ATP Detection Reagent to all wells and the luminescence of all samples was measured by an Infinite F200 plate reader (Tecan).

Figure 2:
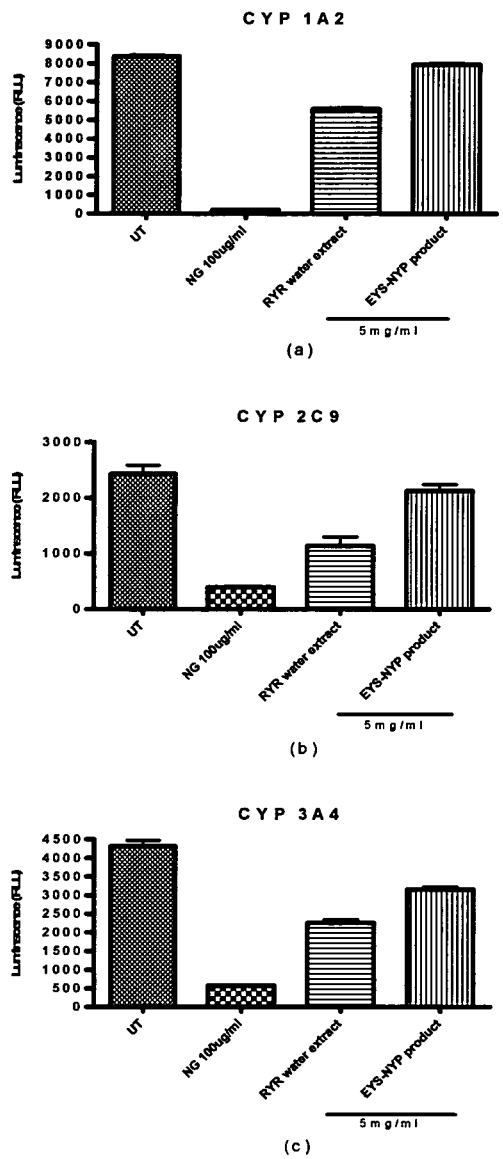
FIG. 2. shows the results of a cytochrome P450 inhibition study using a red yeast rice extract.

The luminescence signal observed in the CYP activity assay was directly proportional to the enzyme activity. The net signals from untreated CYP reactions represent total CYP activity. 100 μg/ml of naringenin (a CYP inhibitor) was added as negative control for the experiment. Changes from the average net signal of untreated CYP reactions for reactions with the test compound (RYR water extract) demonstrate the modulation of CYP activity by this compound. The luminescence signal for the testing compound is higher than the untreated samples demonstrating that this compound can enhance CYP activity; the luminescence signal lower than the untreated samples implying this compound could inhibit the activity of CYP. The results (FIG. 2) demonstrate that the RYR water extract induces inhibition of CYP1A2, CYP2C9 and CYP3A4. The EYS-NYP product, which is the RYR extract obtained after removal of the polar compounds, demonstrates very low inhibition of CYP activity.

P-Glycoprotein (P-Gp) Activity Study

An enzyme kit, Pgp-Glo™ Assay System (Promega, USA) was used to analysis the influence of RYR water extracts on P-gp activity. This assay detects the effects of compounds on recombinant human P-gp in a cell membrane fraction and relies on the ATP dependence of the light-generating reaction of firefly luciferase. ATP is first incubated with P-gp; then the P-gp ATPase reaction is stopped, and the remaining unmetabolized ATP is detected as a luciferase-generated luminescent signal. P-gp-dependent decreases in luminescence reflect ATP consumption by P-gp; thus the greater the decrease in signal, the higher the P-gp activity. Accordingly, samples containing compounds that stimulate the P-gp ATPase will have significantly lower signals than untreated samples. Preparations of P-gp, the reaction mixture and ATP detection reagent were followed according to the manufacturer's instructions. 20 μl of RYR water extract was prepared at different concentrations (1.25, 2.5 and 5 mg/ml), verapamil (positive control, 0.5 mM) and $Na_3VO_4$ (a P-gp inhibitor, 0.25 mM) were added into a white opaque 96-well plate (with clear flat bottom, Costar Inc, NY) respectively. P-gp was then added into wells containing the testing compounds and incubated at 37° C. for 5 min. The reactions were initiated by addition of Mg-ATP solution, the 96-well plate was incubated at 37° C. for 40 min. The reactions were then stopped, and detection of luminescence was initiated by adding the ATP Detection Reagent to all wells and measuring the resulting luminescence on an Infinite F200 plate reader (Tecan, Austria).

Figure 3:
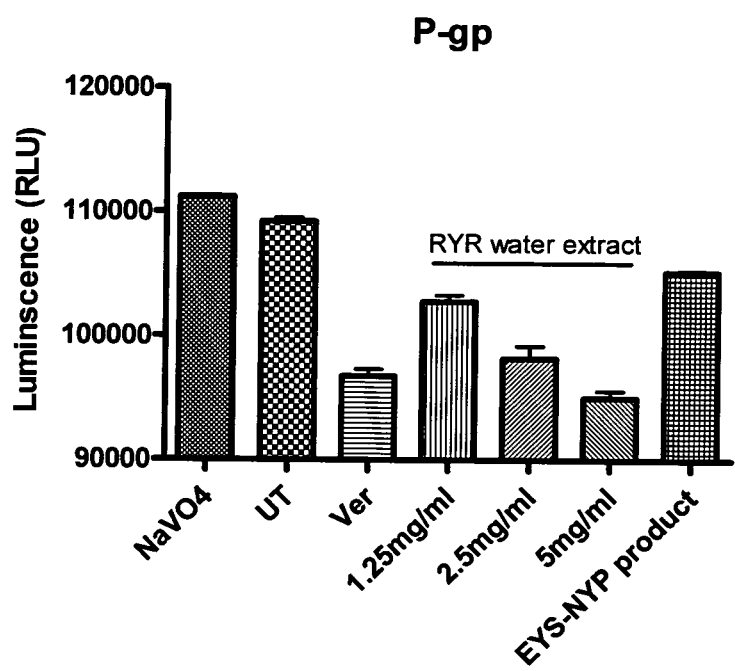
FIG. 3. shows the results of the activity of polar compounds on P-glycoprotein with a negative control ($NaVO_4$)

In the P-gp activity assay, the effect of RYR water extract on Pgp ATPase activity was examined by comparing the untreated samples (basal) and samples treated with RYR water extract to a $Na_3VO_4$ (sodium orthovanadate)-treated control (see FIG. 3). $Na_3VO_4$ is a selective inhibitor of P-gp, and samples treated with $Na_3VO_4$ have no P-gp ATPase activity. In the absence of $Na_3VO_4$, basal and drug-stimulated P-gp ATPase activities can be detected. ATP consumption in the presence of $Na_3VO_4$ is attributed to minor non-P-gp ATPase activities present in the membrane preparation. The differences in luminescent signal between. $Na_3VO_4$-treated samples and untreated samples represents the basal P-gp ATPase activity; while the difference in the luminescent signal between $Na_3VO_4$-treated samples and samples treated with the test compound (RYR water extract) represents P-gp ATPase activity in the presence of the test compound.

Figure 4:
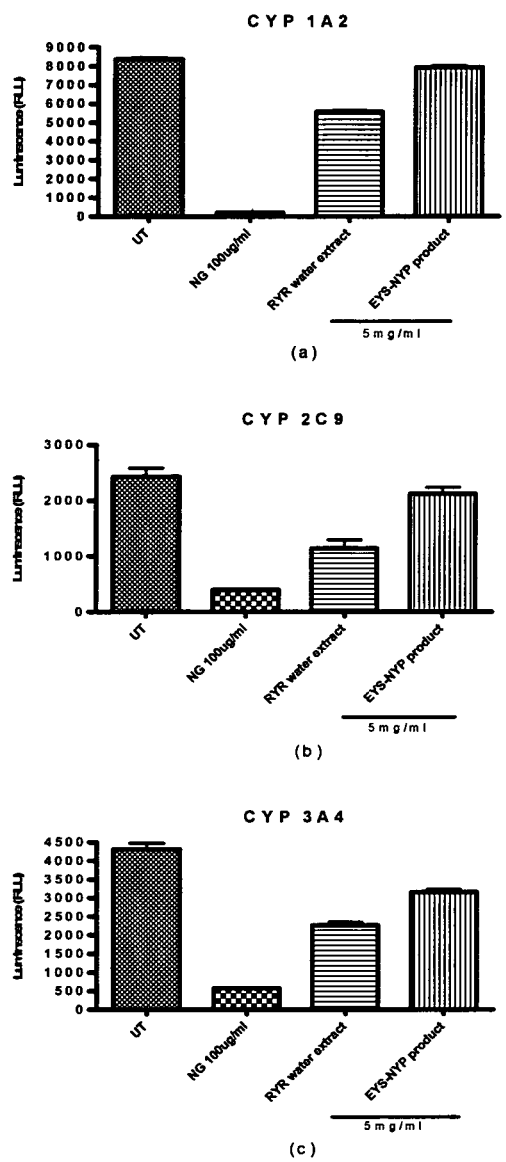
FIG. 4. shows the results of a P-gp activity assay using red yeast rice extract.

As shown in FIG. 4, addition of RYR water extract significantly enhanced P-gp activity and the activation was dose-dependent. These results suggested that RYR water extract contains a P-gp substrate, when it was incubated with the P-gp membrane, ATP was consumed by the P-gp, and a strong change in luminescence when comparing with the Na3VO4-treated samples was observed. The EYS-NYP product shows relatively low activation of P-gp activity, this implies that the compounds in RYR which could influence P-gp activity were removed effectively by the method.

CaCo-2 Absorption Assay

Flasks which were 90-100% confluent were harvested with trypsin/EDTA, neutralized with serum-containing medium, and centrifuged. The cell pellet was resuspended in a serum-free medium consisting of a Basal Seeding medium (BD Biosciences) and Mito$^+$ Serum Extender (BD Biosciences) and seeded onto 6-well Cell Culture Inserts (Corning, N.Y.) at $6\times10^5$ cells/cm2. The inserts contain a polyester 0.4 µm microporous membrane with collagen type I. The seeding medium was replaced 24 hours after cell seeding with Enterocytes Differentiation medium (BD Biosciences) in experiments, which required use of differentiation medium; the medium was replaced every 48 hours thereafter and the cells were maintained at 37° C., 95% relative humidity, and 5% $CO_2$. After three days incubation in the Enterocytes Differentiation medium the CaCo-2 monolayers were ready for permeability studies.

Physiologically and morphologically well-developed CaCo-2 cell monolayers with transepithelial electrical resistance (TEER) values greater than 300 $\Omega cm^2$ were used for the studies.

The transport medium used for these studies was modified Han's buffer containing 10 mM HEPES. The pH of both the apical and basolateral compartments was 7.5. Prior to all experiments, each monolayer was washed twice with buffer and TEER was measured to ensure the integrity of the monolayers. The apical to basolateral (A to B) transport of verapamil was measured in the absence and presence of the test compound. The concentration of verapamil used was 100 µM, which was much below its $K_m$ value of ~60 µM. The concentration of test compounds was chosen to be 10 µM in this assay. The studies were initiated by adding an appropriate volume of buffer containing digoxin to either the apical (A to B transport) or basolateral (B to A transport) side of the monolayer. The volumes of the apical and basolateral compartments were 1.6 and 2.8 ml, respectively, and the test compound (as an inhibitor) was added to both sides of the monolayer at a concentration of 10 µM. The monolayers were then incubated for 3 hours at 37° C. Samples are taken from the basolateral compartment at 0 min, 10 min, 30 min, 60 min, 90 min, 120 min and 180 min; and from the apical compartment at 0 min respectively, during the incubation period and analyzed for concentrations of verapamil by HPLC. The A to B permeability coefficient ($P_{eff}$) of verapamil was calculated in the presence and absence of the test compound.

Figure 5:
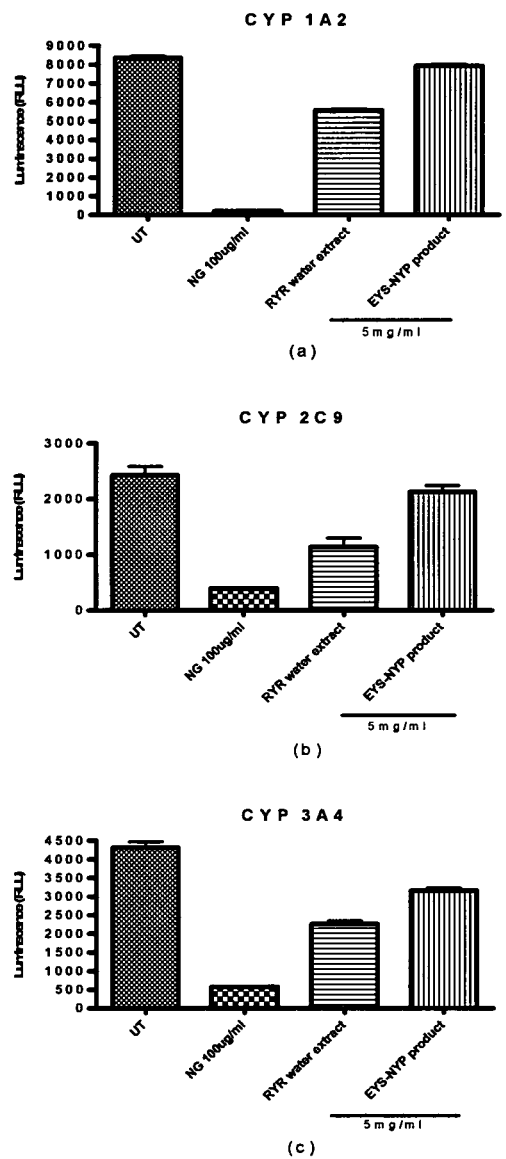
FIG. 5 shows the results of a CaCO-2 absorption study with verapamil using red yeast rice extract, and FIG. 6. shows the results of an animal absorption study using verapamil using red yeast rice extract.

After investigation on the effects of RYR water extract on enzyme level (P-gp and CYP assay), CaCo-2 absorption assay was employed to analyze the effect of RYR water extract in cell level. In vitro studies with CaCo-2 cell monolayers are valuable tool for predicting human in vivo intestinal permeability. In the experiments, 50 µl of 1×PBS (control) or RYR water extract at various concentrations (20 mg/ml and 50 mg/ml, drug treated) were added into the apical compartment of the tissue culture plates with verapamil at 100 µg/ml. The concentrations of the samples taken from the basolateral and apical compartments were calculated from a calibration curve (data not shown) which was constructed by measuring the peak area obtained from injections of verapamil standards (259 µg/ml, 125 µg/ml, 30 µg/ml, 15 µg/ml, 7.5 µg/ml and 3 µg/ml) and the regression analysis linear equation was y=27043x−11153 ($r^2$=0.098). RYR water extract enhance (2-fold) the net absorption of verapamil in the CaCo-2 study. However, the EYS-NYP product (produced in accordance with the method of the disclosure) shows similar results as the control. This demonstrated that the method was able to remove the polar compounds that effect pharmacokinetics of a drug in a subject in RYR effectively (FIG. 5).

Animal Study

Male Sprague-Dawley rats weighting 200-270 g were purchased from Animal House of National University of Singapore (NUS, Singapore). Rat care was in accordance with institutional guidelines. The animals were housed in conventional conditions under controlled cycles of darkness/light (12 hr/12 hr) with a regulated temperature (25° C.). Eight rats were allocated into two groups (2×4 animals) with four trial runs in each group.

The rats were pretreated with either of 1 ml of 100 mg/ml of RYR polar extracts (pretreated group) or 1 ml of saline (control group) for 30 minutes, and then the animal was given 10 mg/kg of verapamil orally: The rats were anesthetized with ketamine & xylazine (both at 100 mg/ml). Blood samples were collected from the jugular vein at 0, 30, 60, 120, 240, 360 and 480 minutes after drug administration into a 1.5 ml eppendorf tube, and subjected to immediate centrifugation at 13,000 rpm for 2 minutes. The clear plasma layers were transferred to a clean tube and then equal volume of acetonitrile was added to remove protein from the samples. After a brief mix with a vortex, the samples were centrifuged at 13,000 rpm for 2 minutes; the supernatants were transferred into HPLC vials and then analyzed for their verapamil content by HPLC. The peak area ratio for an unknown sample was converted to concentration by reference to a calibration curve of verapamil constructed with a drug-free pooled rat plasma sample.

Figure 6:
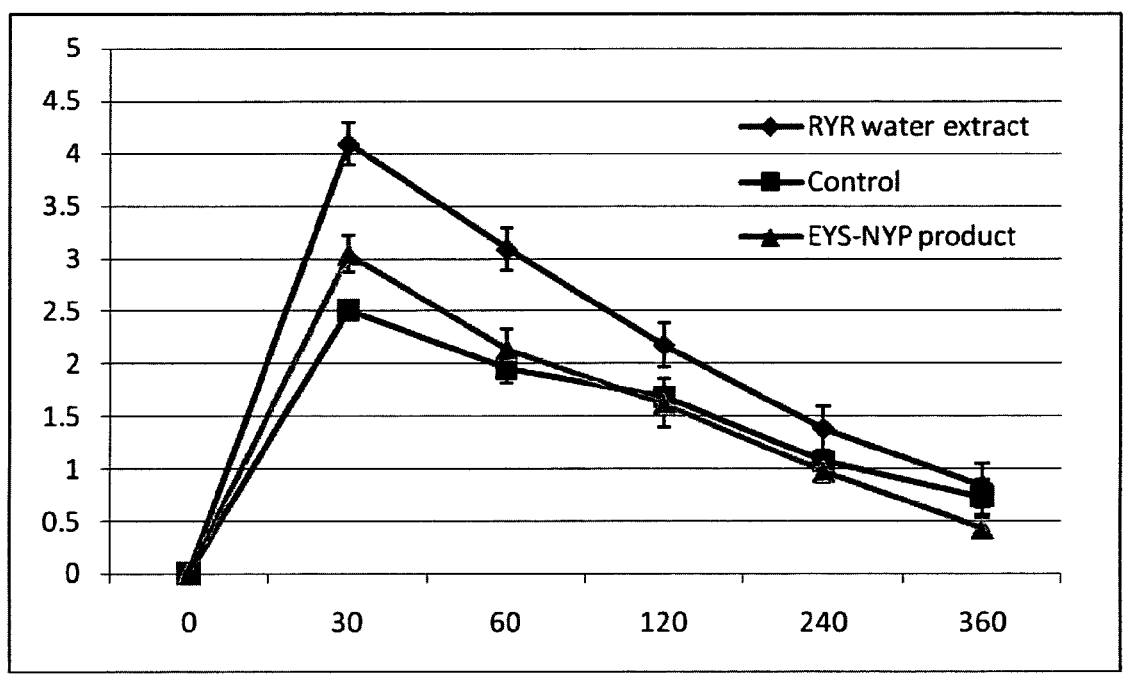

Addition of RYR water extract enhanced absorption of verapamil in the animal model significantly. At the 30 min time point, the level, of verapamil in the drug-treated animal showed about a 1.6 fold higher absorption than the control group and the RYR extract which had the polar compounds removed (EYS-NYP sample) (FIG. 6).

Summary

The method of the disclosure demonstrates the effective removal of one or more polar compounds which affect the pharmacokinetics of a drug in a subject. In the examples above, it has been demonstrated that the one or more polar compounds significantly increases the uptake of verapamil. Verapamil is an L-type calcium channel blocker of the phenylalkylamine class. It is used in the treatment of hypertension, angina pectoris, cardiac arrhythmia. Verapamil overdose symptoms include: low blood pressure (hypotension); a slow heart rate (bradycardia); an irregular heart rhythm (arrhythmia) and fluid in the lungs.

Accordingly, this unexpected drug-herb interaction is potentially life threatening for subjects taking RYR extract in an attempt to improve cardiovascular health by reducing lipids and cholesterol.

APPLICATIONS

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method of preparing an extract from red yeast rice comprising one or more statins, comprising the steps of:
    (a) treating the red yeast rice with an aqueous solution to remove one or more toxins from the red yeast rice;
    (b) treating the red yeast rice with water, in which polar compounds are soluble;
    (c) removing the water added to the red rice yeast in steps (a) and (b), thereby removing the polar compounds from the red yeast rice, to yield the extract, wherein the extract comprises one or more statins and has polar compounds in an amount less than 30% by weight of the total polar compounds present in the red yeast rice; and
    (d) processing the extract of step (c) into a product.

2. The method as claimed in claim 1, further comprising:
    treating the extract of step (c) and any remaining red yeast rice with an organic solution to yield an organic solvent extract.

3. The method as claimed in claim 2, further comprising the step of:
    (a) separating any remaining red yeast rice from the organic solvent extract; and
    (b) evaporating the organic solvent to form a second dried extract.

4. The method as claimed in claim 1, wherein at least 95% of the polar compounds are removed from the red yeast rice in the water extraction, to yield the extract.

5. The method of claim 1, wherein the aqueous solution comprises a salt selected from the group consisting of sodium phosphate, sodium acetate, and sodium bicarbonate.

6. The method of claim 1, wherein the aqueous solution comprises an organic acid.

7. The method of claim 1, wherein the aqueous solution comprises a carboxylic acid.

8. The method of claim 1, wherein the aqueous solution is water.

9. A method of preparing an extract from red yeast rice comprising one or more statins, comprising the steps of:
    (a) treating the red yeast rice with an aqueous solution to remove one or more toxins from the red yeast rice;
    (b) removing the aqueous solution;
    (c) treating the red yeast rice with water, in which polar compounds are soluble;
    (d) removing the water added to the red yeast rice in step (c), thereby removing the polar compounds from the red yeast rice, to yield the extract, wherein the extract comprises one or more statins and has polar compounds in an amount less than 30% by weight of the total polar compounds present in the red yeast rice; and
    (e) processing the extract of step (d) into a product.

\* \* \* \* \*